(12) United States Patent
Cranfill, III et al.

(10) Patent No.: US 8,274,038 B2
(45) Date of Patent: Sep. 25, 2012

(54) DUST CONTROL AND FLOW CONTROL TESTING DEVICE AND METHOD OF REDUCING AIRBORNE DUST AND INCREASING FLOW OF BULK MATERIALS

(75) Inventors: John C. Cranfill, III, Lexington, KY (US); John C. Cranfill, Jr., Pewee Valley, KY (US); Kenneth D. Burnside, Fort Myers, FL (US)

(73) Assignee: AKJ Industries, Inc., Fort Meyers, FL (US)

( * ) Notice: Subject to any disclaimer, the term of this patent is extended or adjusted under 35 U.S.C. 154(b) by 507 days.

(21) Appl. No.: 12/637,094

(22) Filed: Dec. 14, 2009

(65) Prior Publication Data
US 2011/0140012 A1 Jun. 16, 2011

(51) Int. Cl.
*H01J 40/14* (2006.01)
*G01N 21/85* (2006.01)
(52) U.S. Cl. .................... 250/222.2; 250/573
(58) Field of Classification Search ............... 250/222.2, 250/573, 574, 222.1, 221, 214 R, 214.1, 231.1; 356/300, 336, 337, 341, 338, 339, 343, 426, 356/427, 433, 436, 213, 229, 218, 234; 73/28.04, 73/28.01, 31.03, 31.07, 863.21, 432.1, 864.43
See application file for complete search history.

(56) References Cited

U.S. PATENT DOCUMENTS

| | | | | | |
|---|---|---|---|---|---|
| 3,376,753 | A | * | 4/1968 | Pitkin et al. | 73/866 |
| 3,390,424 | A | * | 7/1968 | Fortune | 425/145 |
| 4,667,887 | A | * | 5/1987 | Kawaguchi | 241/20 |

* cited by examiner

*Primary Examiner* — Que T Le
*Assistant Examiner* — Jennifer Bennett
(74) *Attorney, Agent, or Firm* — Marshall, Gerstein & Borun LLP

(57) ABSTRACT

A method for determining quantity and/or a type of dust control agent for controlling dust of a bulk material or flowability thereof comprises dispensing a bulk material into an agitator and agitating the bulk material in the agitator to create airborne dust from the bulk material. A test method for determining a quantity and/or a type of dust control agent effective for reducing a quantity of airborne dust that separates from a bulk material during handling comprises: 1) dispensing a dust-containing bulk material into an agitator; 2) agitating the bulk material in the agitator to a degree sufficient to produce airborne dust from the bulk material; and 3) measuring a quantity of airborne dust produced from the bulk material; repeating steps 1), 2) and 3) after applying a particular dust control agent to said bulk material; and comparing the quantity of airborne dust that separates from the bulk material with and without the dust control agent.

13 Claims, 5 Drawing Sheets

DUST CONTROL AND FLOW CONTROL TESTING DEVICE AND METHOD OF REDUCING AIRBORNE DUST AND INCREASING FLOW OF BULK MATERIALS

FIELD OF THE INVENTION

The present invention relates to dust control testing method and apparatus. More specifically, the invention is directed to methods of and apparatus for testing properties of particular bulk materials that contain dust, and determining a type and quantity of dust control agent, and/or flow control agent, to apply to the dust-containing bulk material, based on data collected from the test materials and apparatus.

BACKGROUND

Various compositions are used for inhibiting dust of bulk materials from becoming airborne, such as coal and other minerals. A high dust level in air is explosive, leads to respiratory health issues, and represents a loss of bulk material product. However, the amount and type of dust control agent applied to the bulk material to inhibit the dust from becoming airborne varies for different types of bulk material and for different flow rates and conveying apparatus used to move the bulk material.

Another issue with bulk materials relates to the potential flow rate of the materials. If the flow rate of bulk materials can be increased, or pluggage eliminated or minimized processes and apparatus used to feed the bulk materials would be more efficient and less costly. The processes and apparatus described herein are directed to dust reduction and/or enhancing the flow rate of bulk materials.

Prior art dust-testing materials and apparatus are described below.

PCT/KR00/00351 (WO 00/63669) describes a dust tester for measuring a dust content, which is generated when tissue sheets are pulled up from a carton, comprising a suction means for forcibly suctioning air containing the dust generated from the carton and a filtering means for filtering the dust of the air suctioned by said suction means.

CN21180560Y describes a foam dust removal system used for coal mines underground. A foaming agent is added into a water pipe through a small-flow quantitative adding pump. A mixed liquid containing a foaming agent and compressed air pass through the foam maker, so as to generate a large amount of foam. The foam is sprayed in an umbrella shape, thereby covering a dust producing point.

CN1746261A describes an anti-explosion and dust-settling agent for coal gas consisting of dioctyl diacid 5-200, fire-retardant TDCPP 5-200, Span 5-300, cholamine 5-200, sodium dodecyl benzene sulfonate 60-800, emulsifier 20-400, Tween 5-300, sodium hydrogen carbonate 16-80, peppermint oil 3-15, vitamin B61-15 and water 1000-50000.

There is a need, however, for a method for determining a quantity and a type of dust control agent that would be effective in reducing dust in bulk materials, such as coal, coke, and limestone during handling, such as on a conveyor belt.

SUMMARY

The dust testing methods and apparatus described herein utilize quantitative data collected from the weight of coal dust collected in a filter, and, in a preferred embodiment, uses readings from a TSI DustTrak monitor, to determine the type and amount of "dust control agent" to apply; and in another embodiment, the duration of the test is monitored to determine flow rates, and the amount of material passed through the device is weighed.

The weight of coal dust collected in the filter is determined by weighing the filter prior to the test and weighing it again after the test.

The DustTrak device is an aerosol monitor. It utilizes a laser photometer that simultaneously measures both mass and size fraction of dust contained in air.

Each test is run using a fixed amount of coal. The time required, or duration of the test, is measured to determine the rate of coal flow. The shorter the time it takes for a known quantity of coal to go through the testing device, the higher is the flow rate of the coal.

DETAILED DESCRIPTION

Figure 1:
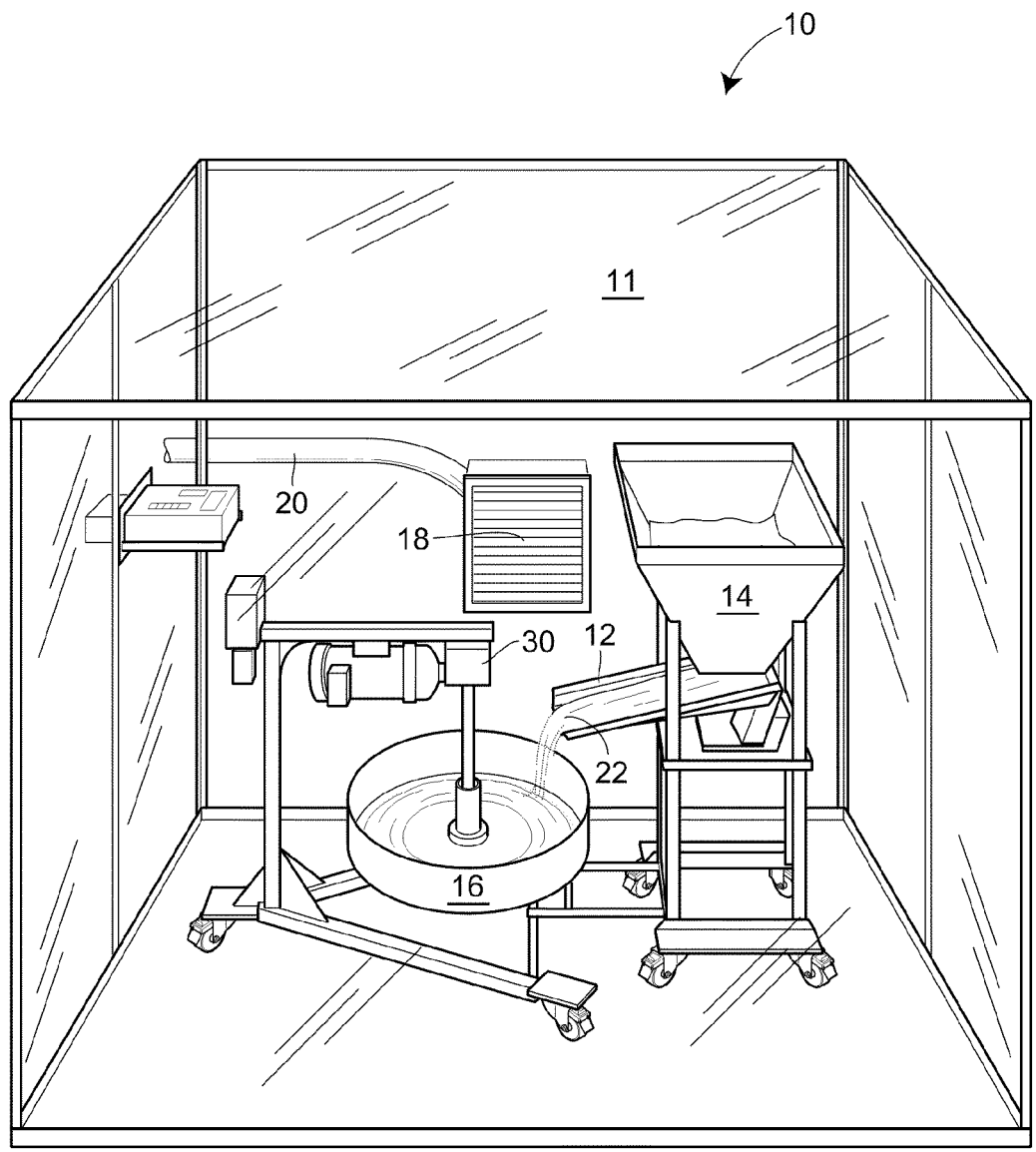
FIG. 1 is a perspective view of the bulk material dust control testing apparatus enclosed within a transparent housing.
Figure 2:
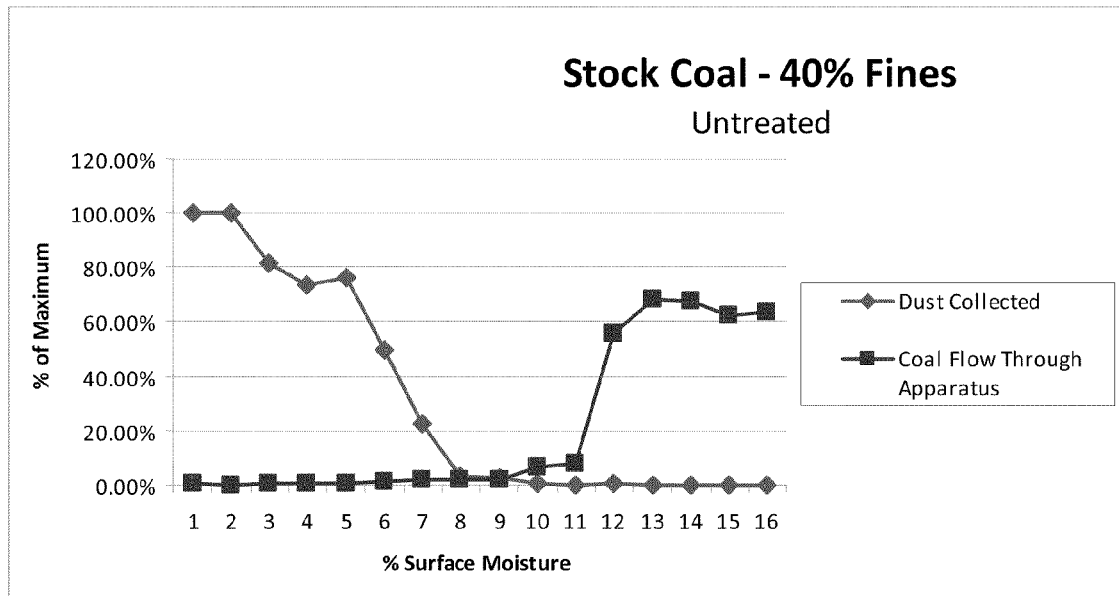
FIG. 2 is a graph showing wt. % of dust recovered and relative speed of coal flowing through the testing apparatus of FIG. 1 vs. coal surface moisture for untreated coal.
Figure 3:
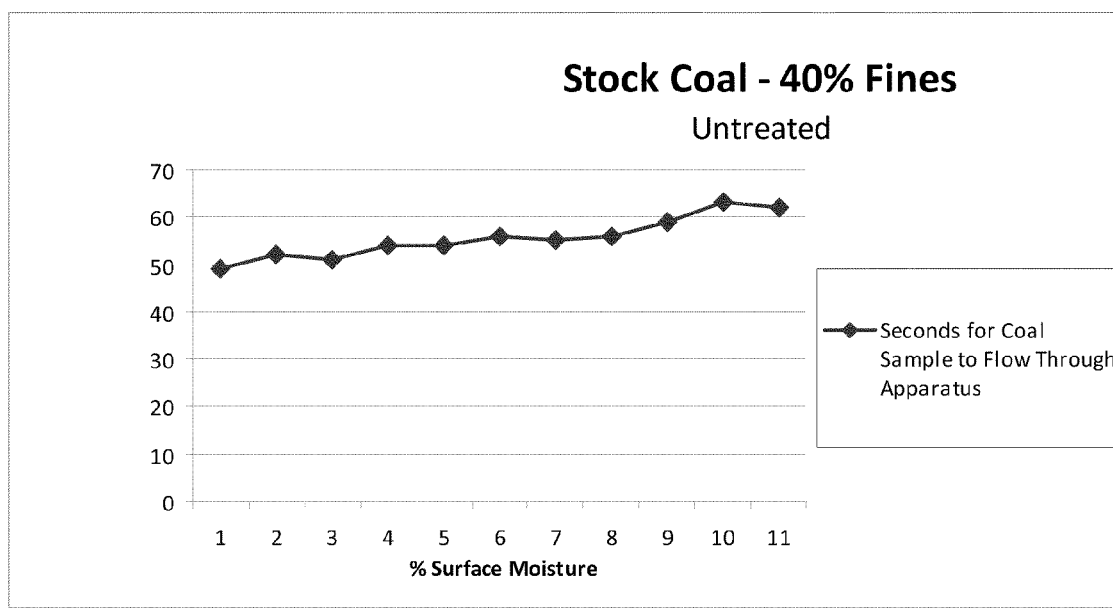
FIG. 3 is a graph showing the number of seconds for a coal sample to flow through the apparatus of FIG. 1.
Figure 4:
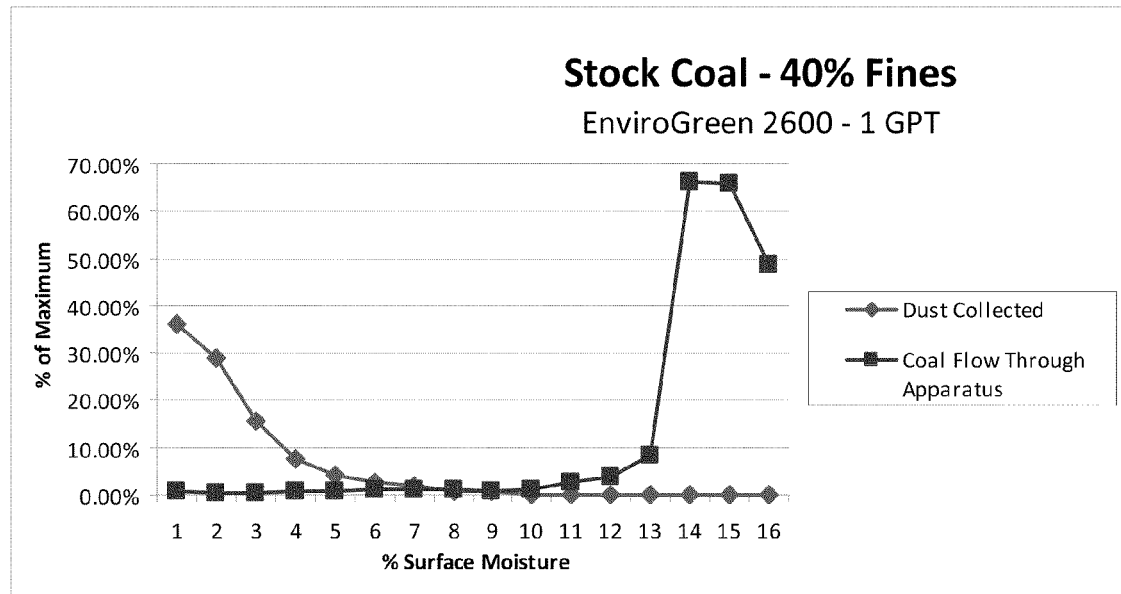
FIG. 4 is a graph showing wt. % of dust recovered and relative speed of coal flowing through the testing apparatus of FIG. 1 vs. coal surface moisture for coal treated with EnviroGreen 2600.
Figure 5:
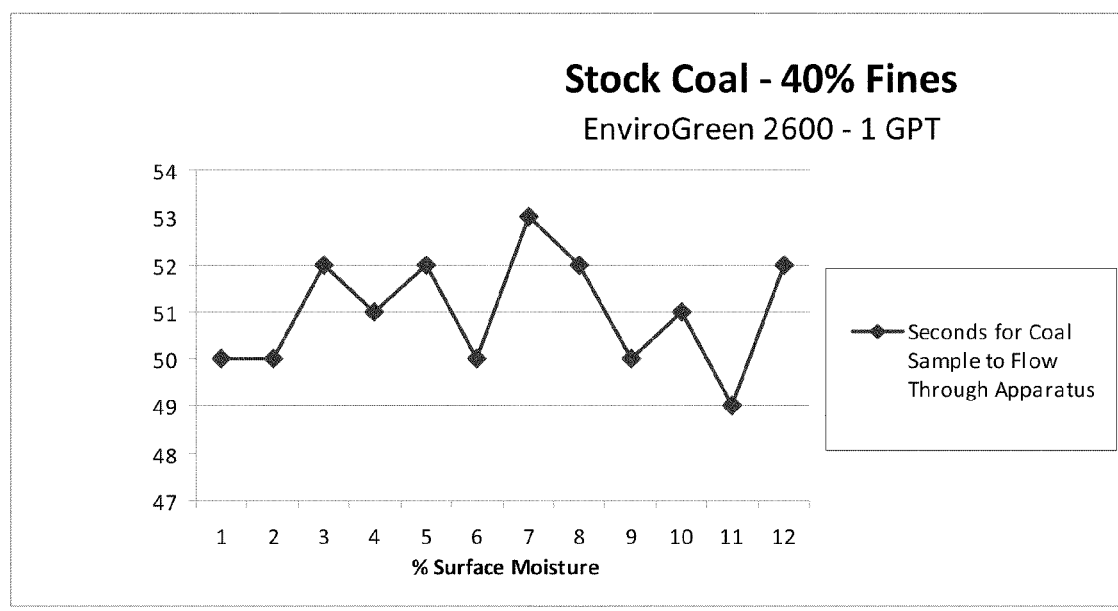
FIG. 5 is a graph showing the number of seconds for a coal sample to flow through the apparatus of FIG. 1 vs. coal surface moisture for coal treated with EnviroGreen 2600.
Figure 6:
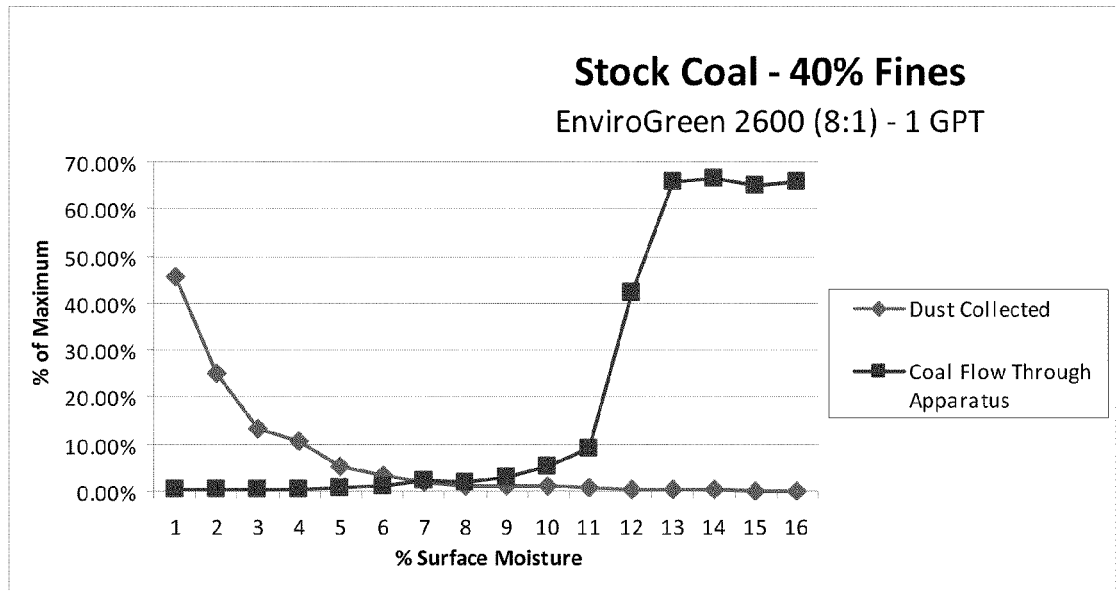
FIG. 6 is a graph showing wt. % of dust recovered and relative speed of coal flowing through the testing apparatus of FIG. 1 vs. coal surface moisture for coal treated with diluted EnviroGreen 2600.
Figure 7:
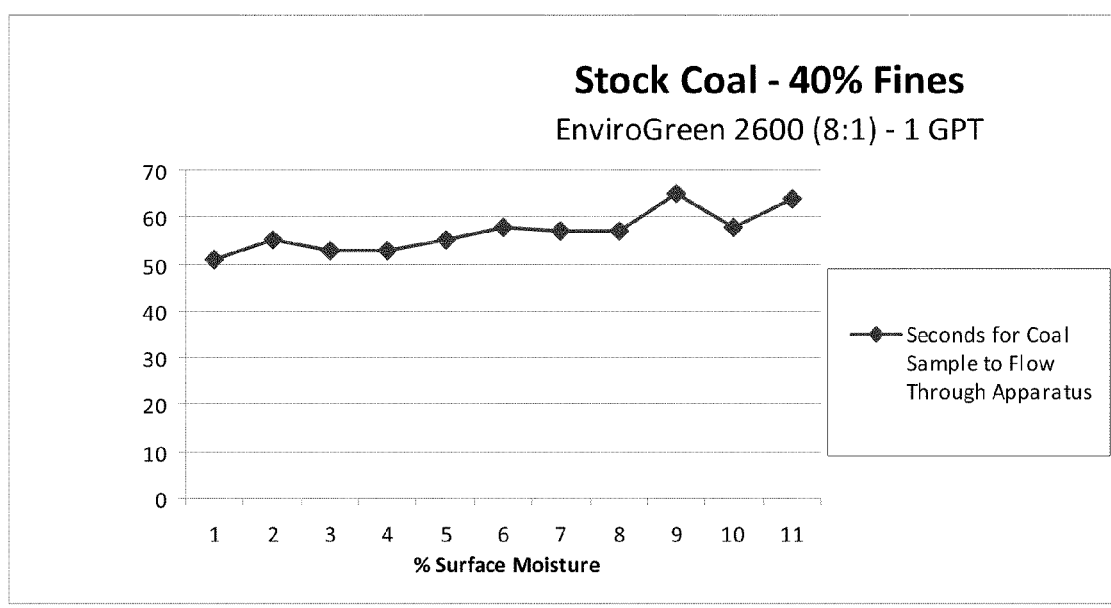
FIG. 7 is a graph showing the number of seconds for a coal sample to flow through the apparatus of FIG. 1 vs. coal surface moisture for coal treated with diluted EnviroGreen 2600.
Figure 8:
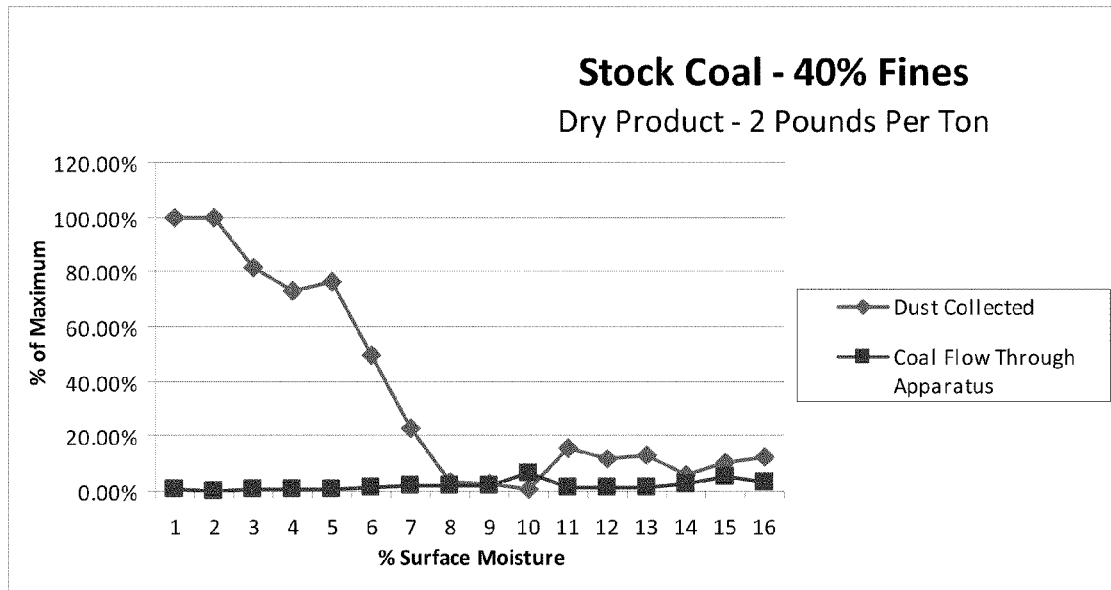
FIG. 8 is a graph showing wt. % of dust recovered and relative speed of coal flowing through the testing apparatus of FIG. 1 vs. coal surface moisture for coal treated with a dry, prior art superabsorbent polyacrylate.
Figure 9:
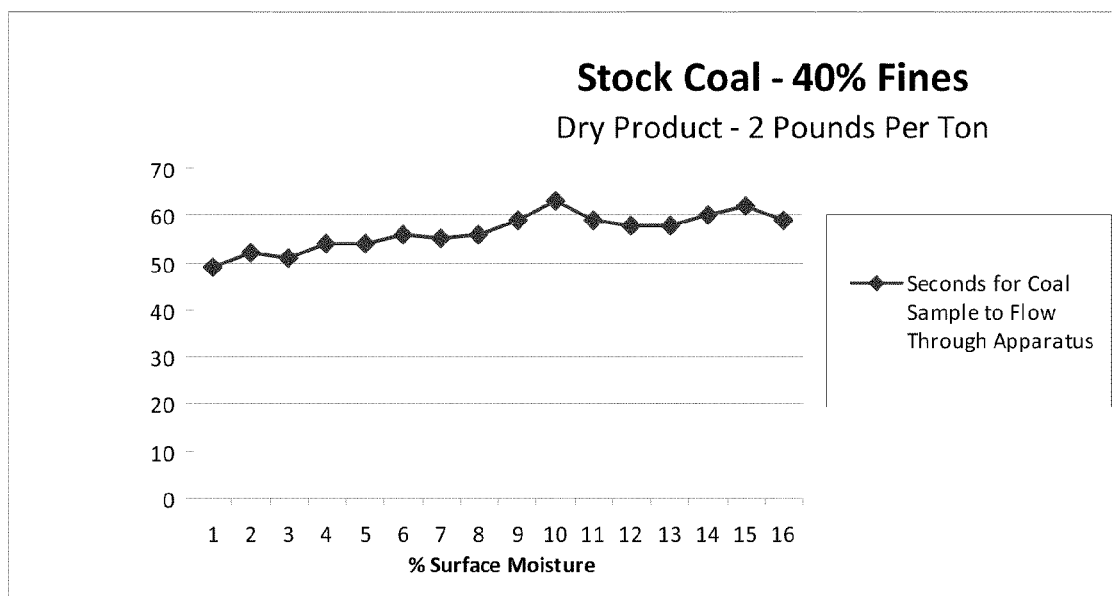
FIG. 9 is a graph showing the number of seconds for a coal sample to flow through the apparatus of FIG. 1 vs. coal surface moisture for coal treated with a dry superabsorbent polyacrylate.

The amount and type of dust control agent that may be applied to a dust-containing bulk material, such as coal, coke or limestone, is difficult to determine, particularly for materials that contain different amounts and sizes of dust with each batch of bulk material. Coal dust, for example, has a particle size such that about 75% by weight of the dust particles have a size less than about 75 mm (200 mesh, U.S. Serve Series). Most coal dust (50-70% by weight) has a diameter in the range of about 35 mm to about 210 mm, with about 30-50% by weight of coal dust having a size less than 75 mm. The quantity and size of the dust varies widely in coal obtained from different mixes, in different areas of the world.

In order to determine an effective quantity and type of dust-reducing agent to apply to a bulk material, such as coal, coke or limestone, when it must be handled (moved from one location to another) to reduce dangerous airborne dust, in accordance with the methods and apparatus described herein, the coal is vibrated and isolated using the apparatus shown in the drawings, while catching the airborne dust particles in a filter disposed at an inlet of a vacuum hose, in an enclosed space.

As shown in FIG. 1, the dust control testing apparatus 10 is contained within an enclosed, transparent, e.g., plexi-glass housing 11. The apparatus 10 includes an inclined, vibrating trough or chute 12 disposed below a bulk material hopper 14; a rotating pan 16; and a filter 18 disposed to cover a vacuum hose 20. The dust-containing bulk material, e.g., coal 22, is fed to the vibrating chute 12 from hopper 14 and free falls into the rotating pan 16 that acts as a collection device. At coal transfer points in essentially all coal-using industries, e.g., the utility and steel industries, coal-handling apparatus and methods include the step of coal free-falling onto a moving conveyor belt. Transfer points are often the source of dusting within material-handling units due to the fact that the material is impacted via free fall (often generating dust) and experiences an increase in air velocity while free falling through an enclosed chute (causing the dust to become airborne). The free-fall of coal from the vibrating chute 12 into the rotating pan 16 simulates free-fall onto a moving conveyor belt using the vibrating, inclined chute 12 spaced above the rotating pan 16 which moves the falling bulk material 22, similar to a conveyor belt. The suction hose 20 disposed in fluid communication with in-line filter 18 also has the capacity to control air velocity exiting the enclosed space—through the filter 18, thereby being capable of increasing air velocity in the close proximity to the moving bulk material, similar to an increase in air velocity encountered in industry at bulk material transfer points.

The vibrating chute 12 and rotating pan 16 are both enclosed in the plexi-glass cage 11 in order to trap any generated dust and allow for convenient viewing. The suction hose 20 and inline filter 18 collect generated dust and quantify results.

In accordance with another embodiment described herein, a DustTrak™ device 30 is mounted above the rotating pan 16 used to collect real time dust levels and offer another layer of quantitative data (average and maximum dust levels in mg per cubic meter for each test run, as well as how long each test takes to run).

The first step is to weigh a clean filter 18 before the test is run. This weight is then recorded. The first test is run with an untreated sample of coal 22. The untreated material 22 is loaded into the vibrating chute 12 (at this stage, both the vibrating chute 12 and rotating pan 16 are in the off position and the plexi-glass cage 11 is raised above the equipment). It is important to note that the samples 22 tested have been previously prepared to ensure the size, weight, moisture content, and fines content are consistent from sample to sample. After the material is loaded, the enclosure is lowered into place and the clean filter 18 is secured into position. The suction hose 20 is then turned on and the vibrating chute 12 and rotating pan 16 are activated. The DustTrak device 30 is also put into Sample mode at this time. The vibrating chute 12 feeds material into the rotating pan 16. Once all the material 12 has gone through the device, the vibrating chute 12 and rotating pan 16 are turned off and the DustTrak 30 is stopped. The filter 18 is removed (with the suction hose still activated so that no dust is lost) and weighed to measure the amount of dust collected. Average and maximum dust levels are taken off of the DustTrak 30 as well as the total time it took the coal sample to pass through the vibrating chute. This provides a baseline to test against.

The process described above is repeated for each sample. Subsequent samples are treated with various products at various application rates and dilution ratios.

The device allows testing of multiple products in a quick, convenient and cost effective manner without the expense or time associated with real world trials. These products can be tested to determine how cost effectively they can control dust, as well as how efficiently they allow material to move through a bottleneck. The faster a sample passes through the vibrating chute, the more effective a product is at enhancing flow characteristics.

The device allows testing of specific materials provided by customers to offer detailed information in regards to recommended product, application rates, dilution ratios, and levels of dust reduction and or flow rate increase that can be expected. This is critically important as coal can be very different from one mine or coal user to the next. The testing device permits the user to offer a customized solution based on the coal being treated.

To achieve the most consistent results, the apparatus is enclosed and maintained at ambient temperature and pressure that approximates the ambient conditions where the coal is being processed, e.g., near a coking oven, or near a rail yard where coal is being loaded into a rail car, or near a coal storage silo.

Another common problem in material handling is material flow. Typically associated with moisture, materials often tend to "stick" at certain moisture levels. Each test can be timed in order to determine the effectiveness various dust-control agents or flow enhancing agents have on the flow characteristics of the material being treated.

Applicant's dust-control agent EnviroGreen™ 2600, which is the subject of co-pending provisional application Ser. No. 61/113,693, filed Nov. 12, 2008, hereby incorporated by reference, was tested against untreated coal and water-treated coal using coal from two different sources (Eastern bituminous coals) against untreated coal and water/surfactant-treated coal, as shown in Table 1. For Coal A, surfactant technology yielded an 88% reduction in dust collected while decreasing flow 52%. EnviroGreen 2600 resulted in a 97% reduction in dust collected and improved flow by more than 15%.

For Coal B, surfactant technology yielded an 83% reduction in dust collected while decreasing flow 35%. EnviroGreen™ 2600 (60% glycerin, 0.15% xanthan gum, 2.0% dodecylbenzyl sulfonate surfactant, and 37.85% water) resulted in a 97% reduction in dust collected and improved flow by more than 37%. Glycerin will decrease dust and enhance flow in concentrations of 25 wt. % to about 100. % (neat), preferably about 50 wt. % to about 100 wt. % (neat) when applied to a bulk material surface in an amount of about 1 pint to about 5 gallons, preferably about 0.5 gallon to about 3 gallons per ton of bulk material, based on the dry weight of the bulk material.

Other materials tested, as shown in Tables II and III, included Corn-900, a by-product resulting from the extraction of corn oil from corn; a superabsorbent polymer (SAP), which is a partially crosslinked, partially neutralized sodium polyacrylate used in the manufacture of diapers (as a coal drying material); a liquid bio-fuel manufactured from hay and animal manure as well as other natural feed stocks, such as that described in published U.S. Patent Application 2009/0239279 A1, hereby incorporated by reference; mixtures of mineral salts, such as $CaCl_2$ or $MgCl_2$ and latex, e.g., vinyl acetate copolymers, with and without the above-described xanthan gum solution; water alone; and surfactant alone.

While testing various products to determine their effectiveness as dust control agents on coal, it was noticed that the way in which the coal flowed through the device was significantly altered based on what products were used. In nearly every instance, applying a product that is predominantly water resulted in adverse effects on flow. The effects ranged from slowing down flow to partial or complete plugging of the device. Conversely, some products consistently increased the speed at which the coal flowed through the device and eliminated instances of plugging.

As different coals were tested, it quickly became evident that the predominant factors that effect coal flow are fines content and surface moisture (the presence of clay could also be a contributing factor). Individual coals have a "moisture footprint" that is shaped the same, but ranges across a moisture scale. A typical coal might generate a significant amount of dust at a surface moisture ranging from 0% to 8%. Above 8% the coal may no longer be dusty, but coal flow problems begin to occur in the form of plugged chutes, carry back in (sticking to) railcars, and the like. At a high enough surface moisture, the coal actually turns into a slurry that eliminates both dusting and plugging—however this is typically not an option due to the loss of BTUs from boiler inefficiencies.

To test coal flow, as shown in Tables I-VII and FIGS. 2-13, various coal samples, treated and untreated were tested to see how long a coal sample takes to pass the through a vibrating chute. By comparing treated coal with the untreated samples, trends can be established for each product tested.

To simulate wet coal flow challenges, the surface moisture of coal samples is increased via water addition until the sample will no longer flow through the device. Increasing the moisture content tends to make the coal more cohesive. Cohesive forces acting among wet coal particles are mainly due to capillary forces associated with liquid bridging. Once a sample shows consistent bridging, it can be treated with a product and then run through the device again. The amount of coal that will not pass through the device is measured and compared to the untreated sample.

The type of coal has a significant effect on the flowability because of the differences in their compositions and physical structures. However, significant and repeatable results were obtained with 3 different products.

EnviroGreen 2600 does a very good job at controlling dust on bulk materials, such as coal, coke and limestone, particularly on the lower band of the moisture footprint, e.g., 0 wt. % or 0.01 wt. % to about 11 wt. % water, based on the dry weight of the bulk material. In addition, it serves as a bulk material flow aid by increasing flow speed and reducing pluggage. Statistical evidence indicates that the addition of about 0.05 to about 5% by weight gum, such as xanthan gum, or locust bean gum, preferably about 0.05 wt. % to about 1 wt. %, more preferably about 0.07 wt. % to about 0.2 wt. %. Xanthan gum increases EnviroGreen 2600's ability to control dust. Other useful gums include Agar, Alginic acid, Beta-glucan, Carrageenan, Chicle gum, Dammar gum, Gellan gum, Glucomannan, Guar gum, Gum Arabic, Gum ghatti, Gum tragacanth, Karaya gum, Mastic gum, Psyllim, Sodim alginate, Spruce gum, and Tara gum. Glycerin alone (without the xanthan gum additive or the surfactant) in an aqueous solution, at a concentration of about 25 wt. % to about 100 wt. %, preferably about 50 wt. % to about 100 wt. %, when applied to the bulk material at an application rate of about 1 pint to about 5 gallons, preferably about 0.5 gallon to about 3 gallons, per dry ton of bulk material, also provides positive results as a flow aid and dust control additive, but not to the same degree as the EnviroGreen 2600. The EnviroGreen 2600 and bio-fuel dust control and flow enhancement additives also are applied from aqueous glycerin or biofuel compositions containing about 25 wt. % to about 100 wt. % glycerin of bio-fuel active, preferably about 50 wt. % to about 100 wt. % glycerin or bio-fuel active, at application rates of 1 pint to about 5 gallons, preferably about 0.5 gallon to about 3.0 gallons per ton of bulk material, based on the dry weight of the bulk material.

Bio-Fuel (particularly a Bio-Fuel made from animal manure and hay with 1.5% Surfactant) yielded very similar results to that of EnviroGreen 2600. In a limited test sampling, the addition of Surfactant seems to aid both dust control and coal flow.

Dry Product. Both the Bio-Fuel (with and without surfactant) and the EnviroGreen 2600 performed well until the surface moisture of the coal was too high to overcome (above about 11 wt. %, based on the weight of the coal). In that case, a dry product (a water-insoluble, partially crosslinked, partially neutralized polyacrylate—a superabsorbent polymer or SAP) can be applied to reduce that surface moisture. This product offered very impressive results when tested as a coal flow aid. Application rates of 1 to 3 pounds per ton have been tested. One key difference in the dry product is that it takes time to be effective. At first glance, it seems using the dry product to reduce the surface moisture of the coal enough so that the wet products can be effective would be the most cost effective approach.

TABLE I

| Coal Tested | Product Applied | Dilution Ratio | Application Rate | Filter Weight Before Test | Filter Weight After Test | Dust Collected | Dust Reading (Average) | Dust Reading (Maximum) | Duration of Test |
|---|---|---|---|---|---|---|---|---|---|
| bituminous (Eastern) coal A | Untreated | — | — | 652.3 | 655.7 | 3.4 | 34.800 | 63.300 | 1:47 |
| bituminous (Eastern) coal A | Water/Surfactant | 60:1 | 1.5 gal/ton | 652.8 | 653.2 | 0.4 | 1.100 | 1.610 | 2:43 |
| bituminous (Eastern) coal A | EnviroGreen 2600* | Neat | 1.5 gal/ton | 653.0 | 653.1 | 0.1 | 0.336 | 0.497 | 1:30 |
| Bituminous (Eastern) coal B | Untreated | — | — | 652.3 | 655.9 | 3.6 | 114.000 | 150.00 | 1:15 |
| Bituminous (Eastern) coal B | Water/Surfactant | 60:1 | 1.5 gal/ton | 652.6 | 653.2 | 0.6 | 4.750 | 10.900 | 1:15 |
| Bituminous (Eastern) coal B | EnviroGreen 2600* | Neat | 1.5 gal/ton | 652.8 | 652.9 | 0.1 | 0.800 | 1.180 | 0:47 |

*EnviroGreen 2600: 60 wt % glycerin; 2.0 wt. % surfactant; 0.15 wt. % xanthan gum 37.85 wt. % $H_2O$

TABLE II

AKJ Industries, Inc.
Dust Level Tests to Find Most Effective Products and Application Rates

| Coal Tested | Product Applied | Dilution Ratio (with water) | Application Rate | Maximum Dust Reading | Average Dust Reading | Time | Dust Collected (grams) |
|---|---|---|---|---|---|---|---|
| 40% Fines | No Treatment | | | 150.0 | 47.6 | 52 | 4.2 |
| 40% Fines | No Treatment | | | 150.0 | 81.3 | 54 | 3.9 |
| 40% Fines | No Treatment | | | 150.0 | 62.8 | 50 | 3.8 |
| 40% Fines | No Treatment | | | 150.0 | 71.0 | 50 | 3.9 |
| Averages for untreated samples | | | | 150.0 | 65.7 | 51.5 | 4.0 |
| 40% Fines | Water | Neat | 1 GPT | 81.6 | 28.4 | 49 | 2.2 |
| 40% Fines | Water | Neat | 1 GPT | 71.0 | 19.8 | 53 | 3.1 |
| 40% Fines | Water | Neat | 1 GPT | 56.8 | 22.7 | 55 | 2.4 |
| 40% Fines | Water | Neat | 1 GPT | 73.3 | 26.6 | 50 | 2.1 |
| 40% Fines | Water | Neat | 1 GPT | 79.1 | 24.1 | 52 | 1.8 |
| 40% Fines | Water | Neat | 1 GPT | 122.0 | 21.2 | 52 | 4.3 |
| Averages for samples treated with water | | | | 80.6 | 23.8 | 51.8 | 2.7 |
| 40% Fines | Surfactant CALSOFT L-40% dodecylbenzyl sulfonate, and 60% water | 25:1 | 1 GPT | 10.3 | 4.9 | 47 | 1.1 |
| 40% Fines | Surfactant CALSOFT L-40% dodecylbenzyl sulfonate, and 60% water | 50:1 | 1 GPT | 8.7 | 5.6 | 46 | 1 |
| 40% Fines | Surfactant CALSOFT L-40% dodecylbenzyl sulfonate, and 60% water | 75:1 | 1 GPT | 15.6 | 12.6 | 50 | 1.6 |
| 40% Fines | Surfactant CALSOFT L-40% dodecylbenzyl sulfonate, and 60% water | 100:1 | 1 GPT | 28.1 | 11.3 | 49 | 2.1 |
| Averages for samples treated with Surfactant | | | | 15.7 | 8.6 | 48.0 | 1.5 |
| 40% Fines | CaCl$_2$ (30%)/Latex(70%) | 1:1 | 1 GPT | 19.6 | 12.2 | 51 | 1.5 |
| 40% Fines | CaCl$_2$ (30%)/Latex(70%) | 10:1 | 1 GPT | 29.5 | 15.0 | 56 | 1.8 |
| 40% Fines | CaCl$_2$ (30%)/Latex(70%)/PA (0.1%) | 1:1 | 1 GPT | 12.7 | 6.8 | 52 | 0.7 |
| 40% Fines | CaCl$_2$ (30%)/Latex(70%)/PA (0.1%) | 10:1 | 1 GPT | 18.1 | 9.8 | 52 | 1.5 |
| Averages for samples treated with Latex | | | | 20.0 | 11.0 | 52.8 | 1.4 |
| 40% Fines | Corn-900 | 1:1 | 1 GPT | 52.2 | 21.1 | 55 | 2.9 |
| 40% Fines | Corn-900 | 5:1 | 1 GPT | 47.6 | 28.2 | 50 | 2.1 |
| 40% Fines | Corn-900 | 10:1 | 1 GPT | 61.2 | 27.2 | 53 | 2.4 |
| 40% Fines | Corn-900 | 20:1 | 1 GPT | 91.8 | 33.3 | 56 | 2.5 |
| Averages for samples treated Corn Product | | | | 63.2 | 27.5 | 53.5 | 2.5 |
| 40% Fines | DC-2008 (1.5 wt. % xanthan gum solution) | 10:1 | 1 GPT | 22.8 | 6.4 | 51 | 1.3 |
| 40% Fines | DC-2008 (1.5 wt. % xanthan gum solution) | 15:1 | 1 GPT | 19.8 | 6.1 | 49 | 1 |
| 40% Fines | DC-2008 (1.5 wt. % xanthan gum solution) | 20:1 | 1 GPT | 30.0 | 8.1 | 53 | 1.6 |
| 40% Fines | DC-2008 (1.5 wt. % xanthan gum solution) | 25:1 | 1 GPT | 41.1 | 11.2 | 52 | 1.9 |
| 40% Fines | DC-2008 (1.5 wt. % xanthan gum solution) with Surfactant (2% CALSOFT L-40) | 10:1 | 1 GPT | 11.3 | 3.8 | 48 | 0.7 |
| 40% Fines | DC-2008 (1.5 wt. % xanthan gum solution) with Surfactant (2% CALSOFT L-40) | 15:1 | 1 GPT | 15.9 | 4.7 | 51 | 1.1 |
| 40% Fines | DC-2008 (1.5 wt. % xanthan gum solution) with Surfactant (2% CALSOFT L-40) | 20:1 | 1 GPT | 13.6 | 4.9 | 46 | 0.9 |
| 40% Fines | DC-2008 (1.5 wt. % xanthan gum solution) with Surfactant (2% CALSOFT L-40) | 25:1 | 1 GPT | 19.4 | 6.1 | 50 | 1 |
| Averages for samples treated with xanthan gum solution (and Surfactant in some cases) | | | | 21.7 | 6.4 | 50.0 | 1.2 |
| 40% Fines | MgCl$_2$ (30%) | 10:1 | 1 GPT | 18.9 | 9.6 | 48 | 1.2 |
| 40% Fines | MgCl$_2$ (30%) | 20:1 | 1 GPT | 29.1 | 14.7 | 48 | 1.9 |
| 40% Fines | MgCl$_2$ (30%) 1.5 wt. % xanthan gum | 10:1 | 1 GPT | 15.6 | 8.8 | 49 | 1 |
| 40% Fines | MgCl$_2$ (30%) 1.5 wt. % xanthan gum | 20:1 | 1 GPT | 20.1 | 10.0 | 48 | 1.2 |
| Averages for samples treated with MgCl$_2$ | | | | 20.9 | 10.8 | 48.3 | 1.3 |
| 40% Fines | 60% Glycerin | Neat | 1 GPT | 8.3 | 3.1 | 42 | 1.5 |
| 40% Fines | 60% Glycerin | 3:1 | 1 GPT | 11.4 | 3.5 | 48 | 1.8 |
| 40% Fines | 60% Glycerin | 5:1 | 1 GPT | 11.2 | 4.4 | 47 | 1.8 |
| 40% Fines | 60% Glycerin | 10:1 | 1 GPT | 16.3 | 7.1 | 52 | 2.2 |
| 40% Fines | 60% Glycerin | 25:1 | 1 GPT | 19.5 | 7.1 | 54 | 2.1 |
| 40% Fines | SR-300 (50% glycerin; 0.075% xanthan gum; 49.925% H$_2$O) | Neat | 1 GPT | 5.2 | 1.9 | 42 | 0.4 |
| 40% Fines | SR-300 (50% glycerin; 0.075% xanthan gum; 49.925% H$_2$O) | 3:1 | 1 GPT | 8.1 | 3.5 | 48 | 0.7 |
| 40% Fines | SR-300 (50% glycerin; 0.075% xanthan gum; 49.925% H$_2$O) | 5:1 | 1 GPT | 7.8 | 3.9 | 47 | 0.6 |
| 40% Fines | SR-300 (50% glycerin; 0.075% xanthan gum; 49.925% H$_2$O) | 10:1 | 1 GPT | 12.6 | 5.3 | 49 | 0.9 |

TABLE II-continued

AKJ Industries, Inc.
Dust Level Tests to Find Most Effective Products and Application Rates

| Coal Tested | Product Applied | Dilution Ratio (with water) | Application Rate | Maximum Dust Reading | Average Dust Reading | Time | Dust Collected (grams) |
| --- | --- | --- | --- | --- | --- | --- | --- |
| 40% Fines | SR-300 (50% glycerin; 0.075% xanthan gum; 49.925% $H_2O$) | 25:1 | 1 GPT | 18.1 | 8.1 | 52 | 1.2 |
| 40% Fines | SR-300 (50% glycerin; 0.075% xanthan gum; 49.925% $H_2O$) | Neat | 1 GPT | 4.1 | 1.2 | 41 | 0.3 |
| 40% Fines | SR-300 (50% glycerin; 0.075% xanthan gum; 49.925% $H_2O$) | 3:1 | 1 GPT | 6.1 | 2.8 | 45 | 0.6 |
| 40% Fines | SR-300 (50% glycerin; 0.075% xanthan gum; 49.925% $H_2O$) | 5:1 | 1 GPT | 11.1 | 5.8 | 51 | 0.9 |
| 40% Fines | SR-300 (50% glycerin; 0.075% xanthan gum; 49.925% $H_2O$) | 10:1 | 1 GPT | 21.1 | 9.1 | 53 | 1.4 |
| 40% Fines | SR-300 (50% glycerin; 0.075% xanthan gum; 49.925% $H_2O$) | 25:1 | 1 GPT | 20.1 | 10.0 | 51 | 1.3 |
| 40% Fines | SR-300 (50% glycerin; 0.075% xanthan gum; 49.925% $H_2O$) | Neat | 1 GPT | 4.2 | 0.8 | 40 | 0.2 |
| 40% Fines | SR-300 (50% glycerin; 0.075% xanthan gum; 49.925% $H_2O$) | 3:1 | 1 GPT | 6.1 | 1.1 | 44 | 0.5 |
| 40% Fines | SR-300 (50% glycerin; 0.075% xanthan gum; 49.925% $H_2O$) | 5:1 | 1 GPT | 11.0 | 4.8 | 48 | 0.9 |
| 40% Fines | SR-300 (50% glycerin; 0.075% xanthan gum; 49.925% $H_2O$) | 10:1 | 1 GPT | 11.4 | 4.1 | 47 | 0.9 |
| 40% Fines | SR-300 (50% glycerin; 0.075% xanthan gum; 49.925% $H_2O$) | 25:1 | 1 GPT | 14.0 | 6.8 | 51 | 1.1 |
| Averages for samples treated with glycerin | | | | 11.4 | 4.7 | 47.6 | 1.1 |

TABLE III

| Coal Tested | Product Applied | Dilution Ratio | Application Rate | Dust Collected |
| --- | --- | --- | --- | --- |
| 40% Fines | Corn-900 | 5 to 1 | 1 GPT | 2.7 grams |
| 40% Fines | Corn-900 | 10 to 1 | 1 GPT | 2.9 grams |
| 40% Fines | DC-2008 (SR-300 with 2.0 wt. % CALSOFT L-40) | 15 to 1 | 1 GPT | 1.2 |
| 40% Fines | DC-2008 (SR-300 with 2.0 wt. % CALSOFT L-40) | 10 to 1 | 1 GPT | 0.9 grams |
| 40% Fines | DC-2008 (SR-300 with 2.0 wt. % CALSOFT L-40) | 25 to 1 | 1 GPT | 1.7 grams |
| 40% Fines | $MgCl_2$(30%)/Latex(70%) | 10 to 1 | 1 GPT | 0.6 grams |
| 40% Fines | $MgCl_2$(30%)/Latex(70%) | 20 to 1 | 1 GPT | 1.3 grams |
| 40% Fines | No Treatment | | | 3.8 grams |
| 40% Fines | No Treatment | | | 3.6 grams |
| 40% Fines | No Treatment | | | 4.0 grams |
| 40% Fines | SR-300 50 wt. % glycerine; 0.075% xanthan gum; 49.925% $H_2O$ | 2 to 1 | 1 GPT | 0.7 grams |
| 40% Fines | SR-300 50 wt. % glycerine; 0.075% xanthan gum; 49.925% $H_2O$ | 3 to 1 | 1 GPT | 0.7 grams |
| 40% Fines | SR-300 50 wt. % glycerine; 0.075% xanthan gum; 49.925% $H_2O$ | 5 to 1 | 1 GPT | 0.8 grams |
| 40% Fines | SR-300 50 wt. % glycerine; 0.075% xanthan gum; 49.925% $H_2O$ | 15 to 1 | 1 GPT | 1.1 grams |
| 40% Fines | SR-300 50 wt. % glycerine; 0.075% xanthan gum; 49.925% $H_2O$ | 25 to 1 | 1 GPT | 1.6 grams |
| 40% Fines | SR-300 50 wt. % glycerine; 0.075% xanthan gum; 49.925% $H_2O$ | 8 to 1 | 1 GPT | 0.7 grams |
| 40% Fines | SR-300 50 wt. % glycerine; 0.075% xanthan gum; 49.925% $H_2O$ | 5 to 1 | 1 GPT | 0.9 grams |
| 40% Fines | SR-300 50 wt. % glycerine; 0.075% xanthan gum; 49.925% $H_2O$ | 5 to 1 | 1 GPT | 1.0 grams |
| 40% Fines | SR-300 50 wt. % glycerine; 0.075% xanthan gum; 49.925% $H_2O$ | 10 to 1 | 1 GPT | 0.8 grams |
| 40% Fines | Water | Neat | 1 GPT | 2.2 grams |
| 40% Fines | Water | Neat | 1 GPT | 1.8 grams |
| 40% Fines | Water | Neat | 1 GPT | 1.5 grams |
| 40% Fines | Water | Neat | 1 GPT | 1.7 grams |
| 40% Fines | Water | Neat | 1 GPT | 1.8 grams |

TABLE IV

Stock Coal (40% Fines)
Untreated

| % Surface Moisture | Dust Control | | Wet Coal Flow | |
|---|---|---|---|---|
| | Average Dust Reading | Dust Reading (% of Max) | Average "Stuck" coal | Time |
| 0 | 150 | 100.00% | 0.40% | 49 |
| 1 | 150 | 100.00% | 0.30% | 52 |
| 2 | 122 | 81.33% | 0.40% | 51 |
| 3 | 110 | 73.33% | 0.60% | 54 |
| 4 | 114 | 76.00% | 0.50% | 54 |
| 5 | 74.8 | 49.87% | 1.10% | 56 |
| 6 | 34.1 | 22.73% | 1.70% | 55 |
| 7 | 5.26 | 3.51% | 2.20% | 56 |
| 8 | 3.57 | 2.38% | 1.80% | 59 |
| 9 | 0.86 | 0.57% | 6.60% | 63 |
| 10 | 0.43 | 0.29% | 8.20% | 62 |
| 11 | 0.58 | 0.39% | 55.40% | — |
| 12 | 0.26 | 0.17% | 68.30% | — |
| 13 | 0.15 | 0.10% | 67.40% | — |
| 14 | 0.17 | 0.11% | 62.10% | — |
| 15 | 0.089 | 0.06% | 63.90% | — |

TABLE V

Stock Coal (40% Fines)
EnviroGreen 2600 - 1 Gallon Per Ton

| % Surface Moisture | Dust Control | | Wet Coal Flow | |
|---|---|---|---|---|
| | Average Dust Reading | Dust Reading (% of Max) | Average "Stuck" coal | Time |
| 0 | 54.2 | 36.13% | 0.60% | 50 |
| 1 | 43.1 | 28.73% | 0.40% | 50 |
| 2 | 23.6 | 15.73% | 0.40% | 52 |
| 3 | 11.4 | 7.60% | 0.80% | 51 |
| 4 | 6.12 | 4.08% | 0.90% | 52 |
| 5 | 3.86 | 2.57% | 1.10% | 50 |
| 6 | 2.77 | 1.85% | 1.20% | 53 |
| 7 | 0.912 | 0.61% | 1.10% | 52 |
| 8 | 1.013 | 0.68% | 0.80% | 50 |
| 9 | 0.071 | 0.05% | 1.10% | 51 |
| 10 | 0.014 | 0.01% | 2.60% | 49 |
| 11 | 0.025 | 0.02% | 3.80% | 52 |
| 12 | 0.011 | 0.01% | 8.30% | 54 |
| 13 | 0.011 | 0.01% | 66.20% | — |
| 14 | 0.004 | 0.00% | 65.80% | — |
| 15 | 0.006 | 0.00% | 48.70% | — |

TABLE VI

Stock Coal (40% Fines)
EnviroGreen 2600 (8:1) - 1 Gallon Per Ton

| % Surface Moisture | Dust Control | | Wet Coal Flow | |
|---|---|---|---|---|
| | Average Dust Reading | Dust Reading (% of Max) | Average "Stuck" coal | Time |
| 0 | 68.4 | 45.60% | 0.50% | 51 |
| 1 | 37.6 | 25.07% | 0.50% | 55 |
| 2 | 19.9 | 13.27% | 0.50% | 53 |
| 3 | 15.9 | 10.60% | 0.40% | 53 |
| 4 | 8.19 | 5.46% | 0.60% | 55 |
| 5 | 5.23 | 3.49% | 1.10% | 58 |
| 6 | 2.83 | 1.89% | 2.10% | 57 |
| 7 | 1.755 | 1.17% | 1.90% | 57 |
| 8 | 1.89 | 1.26% | 3.10% | 65 |
| 9 | 1.431 | 0.95% | 5.20% | 58 |
| 10 | 0.918 | 0.61% | 9.30% | 64 |
| 11 | 0.326 | 0.22% | 42.40% | — |
| 12 | 0.451 | 0.30% | 65.80% | — |
| 13 | 0.447 | 0.30% | 66.40% | — |
| 14 | 0.186 | 0.12% | 65.10% | — |
| 15 | 0.104 | 0.07% | 65.80% | — |

TABLE VII

Stock Coal (40% Fines)
Dry Product (Fine) - 2 Pounds Per Ton

| % Surface Moisture | Dust Control | | Wet Coal Flow | |
|---|---|---|---|---|
| | Average Dust Reading | Dust Reading (% of Max) | Average "Stuck" coal | Time |
| 0 | 150 | 100.00% | 0.40% | 49 |
| 1 | 150 | 100.00% | 0.30% | 52 |
| 2 | 122 | 81.33% | 0.40% | 51 |
| 3 | 110 | 73.33% | 0.60% | 54 |
| 4 | 114 | 76.00% | 0.50% | 54 |
| 5 | 74.8 | 49.87% | 1.10% | 56 |
| 6 | 34.1 | 22.73% | 1.70% | 55 |
| 7 | 5.26 | 3.51% | 2.20% | 56 |
| 8 | 3.57 | 2.38% | 1.80% | 59 |
| 9 | 0.86 | 0.57% | 6.60% | 63 |
| 10 | 23.6 | 15.73% | 1.30% | 59 |
| 11 | 17.5 | 11.67% | 1.60% | 58 |
| 12 | 19.3 | 12.87% | 1.50% | 58 |
| 13 | 8.6 | 5.73% | 2.70% | 60 |
| 14 | 15.4 | 10.27% | 5.40% | 62 |
| 15 | 18.3 | 12.20% | 3.40% | 59 |

Table IV is directed to untreated coal and looks at more than just dust control, including wet coal flow. In this round of testing, the coal was air dried until it contained 0% base line surface moisture. Tests were run at this moisture level. The surface moisture was raised in 1% intervals by the addition of water until 15% surface moisture was reached. A battery of tests was run at each moisture level, as shown in Table IV and FIGS. 2-4.

The same testing device was used to test for dust across the range of surface moistures. In addition, the amount of coal that did not pass through the vibrating chute was weighed and recorded to measure for sticking due to wet coal. The time the sample took to run through the device was recorded to analyze flow characteristics Two coal-treatment products were tested—EnviroGreen 2600 and a dry product (partially neutralized, partially crosslinked polyacrylate super absorbent polymer). The EnviroGreen 2600 (EG 2600) was tested with no dilution (Table V) and at a dilution weight ratio of eight parts by weight water to one part by weight EG 2600 (Table VI). The data shows that EG 2600, applied without dilution, offers significant dust control across the moisture curve and reduces problems associated with wet coal flow. When diluted with water (8:1), the EG 2600 solution still offers dust control, but does not act as a coal flow aid. The data clearly shows that the dry SAP product dramatically increases coal flow problems seen at high moisture levels (although, dust levels rise a bit when compared to untreated samples at the same surface moisture).

The data of the Tables and FIGS. 2-9 clearly show the following:

1) The test instrument can clearly identify differences in performance between products on dust control and wet flow;

2) Use of the testing apparatus of FIG. 1 has indicated that a combination of glycerin or Bio-Fuel together with xanthan gum and surfactant provides real differences in dust control and increases coal flow compared to the individual components; and 3) Glycerin or Bio-Fuel alone, without additives, also provides real differences in dust control and increases coal flow.

The invention claimed is:

1. A test method for determining a quantity and/or a type of dust control agent or flow control agent effective for reducing a quantity of airborne dust that separates from a bulk material during handling and/or increases the flow rate of a bulk material during handling comprising the steps of:
   1) dispensing a dust-containing bulk material into an agitator;
   2) agitating the bulk material in the agitator to a degree sufficient to produce airborne dust from the bulk material;
   3) measuring a quantity of airborne dust produced from the bulk material;
   4) repeating steps 1), 2) and 3) after applying a particular dust control agent to said bulk material;
   5) comparing the quantity of airborne dust that separates from the bulk material with and without the dust control agent or flow control agent.

2. The method of claim 1, wherein the quantity of airborne dust is measured by measuring the airborne dust forcibly collected by an air filter, coupled with a suction mechanism, such that the airborne dust is separated from the air as the dust-containing air passes through the filter.

3. The method of claim 1, wherein the quantity of airborne dust is measured with an aerosol dust concentration monitor.

4. The method of claim 1, wherein the quantity of airborne dust is measured by a photometer.

5. The method of claim 2, including the step of simultaneously measuring the quantity of airborne dust in a second, aerosol airborne dust concentration monitor.

6. The method of claim 2, including the step of simultaneously measuring the quantity of airborne dust in a second, photometer airborne dust concentration monitor.

7. A method for determining the application of a quantity and a type of dust control agent or flow control agent for decreasing dust produced during handling or increasing flow of a bulk material comprising:
   1) dispensing a known quantity of a bulk material into a hopper disposed above a downwardly inclined vibrating ramp;
   2) measuring the time required for said known quantity of said bulk material to traverse the vibrating ramp or measuring the dust produced while traversing the vibrating ramp;
   3) repeating steps 1) and 2) after applying a quantity of a particular flow control or dust control agent to said bulk material;
   4) comparing the times or amount of dust collected from steps 2) and 3) to determine if the quantity and type of flow control or dust control agent has increased the flow rate, or quantity of material discharged from the vibrating ramp, or decreased the quantity of dust produced from said bulk material;
   5) and optionally repeating steps 2), 3), and 4) using a different quantity or type of flow control or dust control agent to find a quantity or type of flow control a or dust control agent that further increases the flow rate of or decreases the dust produced from said bulk material.

8. A method for determining a quantity and/or a type of dust control and flow control agent for reducing dust emanating from a bulk material during handling and for increasing flow of the bulk material comprising:
   dispensing a bulk material into an agitator;
   agitating the bulk material in the agitator to create airborne dust from the bulk material;
   measuring the airborne dust concentration created from the bulk material by an airborne dust concentration monitor;
   applying a dust control agent or flow control agent to the bulk material based on the measured airborne dust concentration and again measuring the quantity of dust of the bulk material on a bulk material conveyor to determine whether a reduction of dust has occurred; and
   determining any increase in flow of the bulk material in accordance with the method of claim 7.

9. The method of claim 8, wherein the airborne dust concentration monitor measures the airborne dust concentration by measuring the airborne dust forcibly collected by an air filter coupled with a suction mechanism.

10. The method of claim 8, wherein the airborne dust concentration monitor is an aerosol monitor.

11. The method of claim 8, wherein the airborne dust concentration monitor is a photometer.

12. The method of claim 9, wherein a second airborne dust concentration monitor is an aerosol monitor.

13. The method of claim 9, wherein a second airborne dust concentration monitor is a photometer.

* * * * *